US005092840A

United States Patent [19]

Healy

[11] Patent Number: 5,092,840

[45] Date of Patent: Mar. 3, 1992

[54] VALVED MEDICINE CONTAINER

[76] Inventor: Patrick M. Healy, 401 N. Rossevelt St., Wichita, Kans. 67208

[21] Appl. No.: 552,775

[22] Filed: Jul. 16, 1990

[51] Int. Cl.[5] .......... A61M 37/00

[52] U.S. Cl. .......... 604/83; 604/167; 604/257

[58] Field of Search .......... 604/83, 82, 81, 167, 604/169, 257, 403, 407, 905

[56] References Cited

U.S. PATENT DOCUMENTS

| | | | |
|---|---|---|---|
| 4,406,655 | 9/1983 | Clayton | 604/257 |
| 4,506,691 | 3/1985 | Tseo | 604/83 |
| 4,715,853 | 12/1987 | Prindle | 604/257 |
| 4,871,353 | 10/1989 | Thomsen | 604/83 |
| 4,935,010 | 6/1990 | Cox et al. | 604/167 |
| 5,006,114 | 4/1991 | Rogers et al. | 604/167 |

*Primary Examiner*—John D. Yasko

*Attorney, Agent, or Firm*—Richard K. Thomson

[57] ABSTRACT

A valved medication container for use in a needleless medication transfer system. The provision of a bottle stopper with an integral valve enables a needleless syringe to be utilized to transfer medication from the bottle to a inlet valve of an intravenous tube eliminating the risk of transfer of blood-transmitted diseases between the medication administrator and the patient.

8 Claims, 1 Drawing Sheet

VALVED MEDICINE CONTAINER

BACKGROUND AND SUMMARY OF THE INVENTION

Presently, medication containers, typically bottles, are capped with a rubber-like stopper with a tamper-evident seal surrounding the stopper and at least the upper portion of the container. To administer the medication to the patient, the seal is removed, a syringe with a needle is used first, to puncture the rubber stopper then, to withdraw and administer the proper dosage to the patient.

The use of a needle constitutes a hazard, both to the doctor or nurse administering the medication and to the patient. There is, of course, the risk of inadvertent puncture to both the administrator and the patient as well as the more significant risk of the infection by blood-transmitted diseases between them. With the alarming spread of AIDS as well as the historical spread of hepatitis, one slip by the administrator can have devastating and permanent results.

Injection valves are already in use with intravenous injection tubes, making the use of a needle to inject medication into the patient superfluous. The present invention adds the key and final piece to the puzzle, enabling the utilization of a system for needleless medication transfer: a valved medication container. By using the valved medication container of the present invention, medication can be withdrawn from a container without the necessity of using a needle and injected through the IV flowport, thereby rendering the use, and associated risk of using, a needle obsolete.

Various other features, advantages and characteristics of the present invention will become apparent after a reading of the following detailed description thereof.

BRIEF DESCRIPTION OF THE DRAWINGS

The invention will be better understood when the Detailed Description is read in conjunction with the accompanying drawings in which like items bear like reference numerals and, in which.

DETAILED DESCRIPTION OF THE PREFERRED EMBODIMENTS

Figure 1:
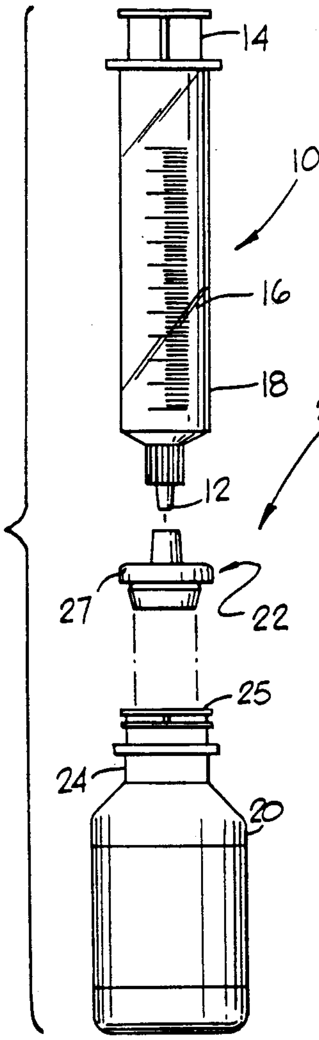
FIG. 1 is an exploded perspective view of the needleless syringe and valved container of the present invention.
Figure 2:
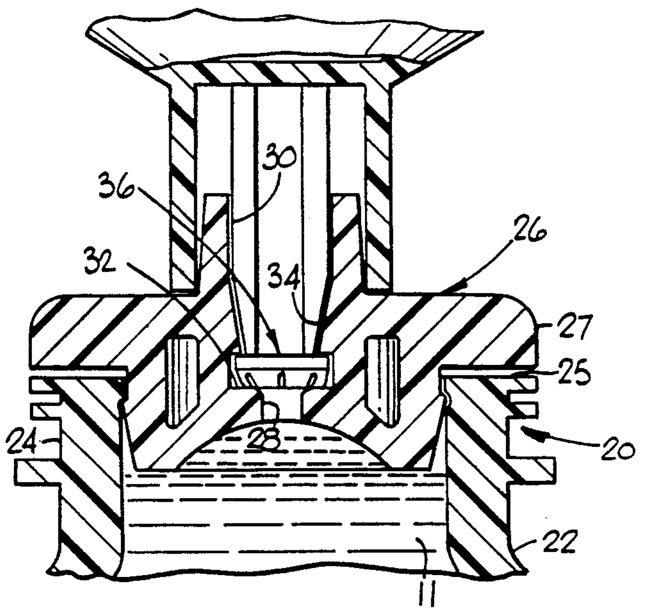
FIG. 2 is an enlarged cross-sectional side view showing the needless syringe engaged with the stopper of the valved container of the present invention.

As shown in the Figures, there are three basic elements to the needleless medication transfer system of the present invention: a needleless syringe 10, a valved medication container 20, and an IV injection valve 40. The syringe may comprise any commercially available syringe including a luer lock type (as depicted in the Figures) or slip connector type syringe. It is the valved medication container 20 that is the novel component of the system and the element which makes the needleless transfer of medication possible.

Syringe 10 is equipped with a blunt tubular leading end 12, includes a plunger 14, and is calibrated with indicia 16 which permits a proper dosage of medication to be withdrawn into the barrel 18 of syringe 10 for transfer to the patient.

Valved medication container 20 includes a bottle 22 which may be any of a number of such standard commercially available bottles. The top mouth portion 24 of bottle 22 receives and is sealed by stopper 26. A portion of stopper 26 fits snugly within mouth portion 24 and may include a rib, or the like, to improve the seal. Flange 27 overlies the top edge 25 of bottle 22. Stopper 26 may be formed of either an elastomeric, rubber-like material or a hard, self-lubricating plastic such as Teflon material. Stopper 26 has a throughbore 28 which connects with a larger withdrawal opening 30. Valve seat 32 protrudes inwardly between throughbore 28 and opening 30. A plurality (which may be two, three, or four) protrusions 34 overlie valve member 36 and retain it in place on valve seat 32.

Valve member 36 is hollow on the lowermost side with a central opening 37 interconnecting slits 38. These slits 38 define flexible fingers 39. In normal position, flexible fingers 39 push the top of valve member 36 against the bottoms of protrusions 34 sealing throughbore 28. When the blunt tubular end 12 of syringe 10 is inserted into withdrawal opening 30, it engages the upper surface of the valve member 36 compressing flexible fingers 39 opening a passageway through central opening 37, slits 38 and out over the top of valve member 36 into syringe 10.

In actual practice, blunt end 12 is inserted into opening 30 with the plunger 14 extended. Air is insufflated (injected) into container 20 to pressurize fluid 11 and facilitate its withdrawal. The plunger can be drawn out of the barrel 18 of syringe 10 (with the container above the syringe) to the position appropriate for the desired dosage as indicated by indicia 16. There is an interference fit between blunt nose end 12 and protrusions 34 to effectively grip the syringe in the stopper during medication transfer to minimize spillage of the medication 11.

Figure 3:
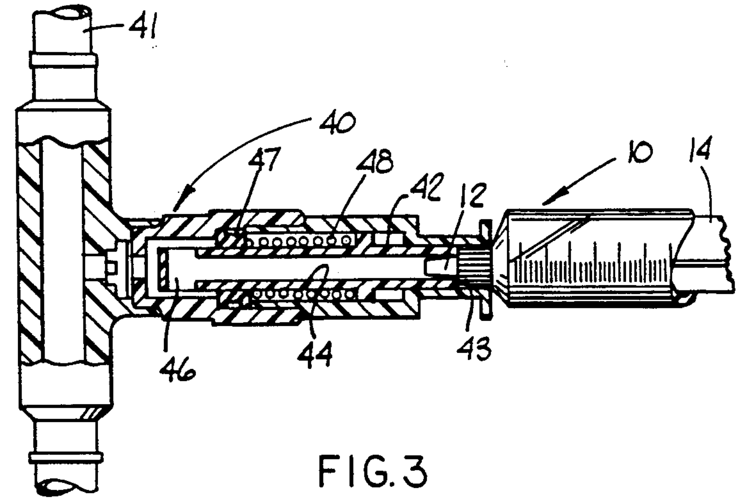
FIG. 3 is a side view in partial section depicting the needleless syringe engaged with an IV injection valve.
Figure 4:
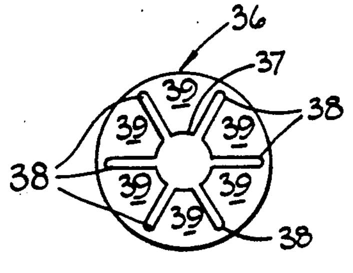
FIG. 4 is a bottom plan view of one valve member which may be used in conjunction with the bottle stopper portion of the valved container of the present invention.
Figure 5:
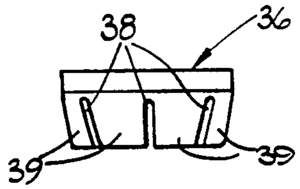
FIG. 5 is a front elevation of the valve member shown in FIG. 4.

Injection valve 40 used on the intravenous injection tube 41 may be any of a number of such valves that are commercially available. By way of example and not limitation, valve 40 may be a "Safeport Injector" available from L & W Technology, Inc. or a "Liferade Line Organizer System" available from Burron Medical Inc. As shown in FIG. 3, injection valve 40 includes a displaceable stem 42 which has a longitudinal throughport 44 with a lateral flowport 46. Stem 42 is normally biased by spring 48 to the right as shown in the drawing to a position where flowport 46 is blocked by cylindrical sleeve 47. In use, blunt nose 12 engages in the upper end 43 of stem 42 displacing it against the pressure of spring 48 opening lateral flowport 46. Medication can then be injected by activating the plunger 14 of syringe 10 completing the needleless transfer of medication from the container 20 to the patient.

The addition of a valved medication container to commercially available injection valve and syringe, completes a system for needleless transfer of medication from container to patient. This significantly reduces the potential for the transfer of blood transmitted diseases between the administrator of the medication and the patient.

Various changes, alternatives and modifications will become apparent to a person of ordinary skill in the art following a reading of the foregoing specification. It is intended that all such changes, alternatives and modifications as fall within the scope of the appended claims be considered part of the present invention.

I claim:

1. A system for transfer of a dosage of medication from a container of said medication to a patient by means of an intravenous tube, said system comprising:

a) a needleless syringe having a blunt tubular leading end;

b) an injection valve in said intravenous tube adapted to receive the blunt leading end of said needleless syringe and permit transfer of said dosage of medication into said intravenous tube; and c) a stopper positioned in a neck portion of said container, said stopper including i) a central throughbore on a first side of said stopper allowing withdrawal of medication from said container;

ii) a valve seat in said stopper;

iii) a valve member received on said valve seat in a first position adapted to close and seal said central throughbore;

iv) an enlarged recess on a second side of said stopper adapted to receive said blunt leading end of said needleless syringe; and v) means associated with one of said valve member and said valve seat which, when engaged by said blunt leading end of said needleless syring, alters the position of said valve member relative to said valve seat to permit insufflation of air into said container and subsequent withdrawal of said dosage of said medication into said needleless syringe.

2. The medication transfer system of claim 1 wherein said second side of the stopper is on a side of said valve which is opposite said first side.

3. The medication transfer system of claim 1 wherein said enlarged recess is concentric with said throughbore.

4. The medication transfer system of claim 1 wherein said stopper further comprises means to retain said stopper in said container.

5. The medication transfer system of claim 4 wherein said means for retaining said stopper in said container includes an annular rib.

6. The medication transfer system of claim 1 wherein the means engaged by said blunt leading end comprises a plurality of protrusions which overlie the valve member and retain said valve member in position on said valve seat.

7. The medication transfer system of claim 6 wherein said means engaged by said blunt leading end of said syringe further comprises an upper surface of said valve member.

8. In a system for permitting needleless transfer of a dosage of medication from a medication container to a patient in order to reduce the chances of injury and the transfer of disease to patient and medication administrator alike, where said system includes a needleless syringe having a blunt tubular leading end, and an injection valve in an intravenous tube injection line for receiving said dosage from said blunt tubular leading end, a stopper for said medication container comprising:

a) a flat disc-shaped portion adapted to overlie a neck portion of said container;

b) a throughbore transiting longitudinally through said stopper, said throughbore permitting withdrawal of medication from said container;

c) a valve seat in said stopper;

d) a valve member received in said valve seat in a first position adapted to close and seal said central throughbore;

e) a cylindrical extension protruding from one side of said disc-shaped portion, said extension defining an enlarged recess adapted for receiving said blunt leading end of said needleless syringe;

f) means associated with one of said valve member and said valve seat which means, when engaged by said blunt leading end of said needleless syringe, alters the position of said valve relative to said valve seat to permit insufflation of air into said container and subsequent withdrawal of said dosage of said medication by said needless syringe for transfer to said injection valve in said intravenous tube injection line.

* * * * *